United States Patent [19]

Fleming

[11] 4,332,723

[45] Jun. 1, 1982

[54] PROCESS FOR PREPARING N-VINYL CARBAZOLES

[75] Inventor: Michael P. Fleming, Boulder, Colo.

[73] Assignee: Syntex (U.S.A.) Inc., Palo Alto, Calif.

[21] Appl. No.: 265,303

[22] Filed: May 20, 1981

[51] Int. Cl.$^3$ .......................................... C07D 209/86
[52] U.S. Cl. .................................... 548/444; 548/445
[58] Field of Search ........................................ 260/315

[56] References Cited

U.S. PATENT DOCUMENTS 2,153,993 4/1939 Reppe et al. ...................... 260/315
3,564,007 2/1971 Stern et al. ......................... 260/315

FOREIGN PATENT DOCUMENTS 641437 8/1950 United Kingdom .

Primary Examiner—Robert W. Ramsuer
Attorney, Agent, or Firm—Howard M. Peters; Joseph I. Hirsch

[57] ABSTRACT

N-Vinyl carbazoles are prepared by reacting an N-unsubstituted carbazole with a dihaloethane in the presence of a phase transfer catalyst followed by reaction with an aqueous solution containing a highly basic agent. These N-vinyl carbazoles are useful, singly or in combination with other materials, as electrical capacitors and insulators, in thermal foam insulators, as components in copolymers and in image-recording systems, and as photoconductive materials in electrophotography.

20 Claims, No Drawings

PROCESS FOR PREPARING N-VINYL CARBAZOLES

BACKGROUND OF THE INVENTION

This invention relates to a process for preparing N-vinyl carbazoles. These compounds have many uses, for example those described by S. Tazuke and S. Okamura in "Vinylcarbazole Polymers" in the *Encyclopedia of Polymer Science and Technology*, Volume 14, page 281 to 304, published in 1971, and references cited therein, all of which are incorporated herein by reference. The preparation of various N-vinyl carbazoles is also described in this reference.

Carbazole has been deprotonated with bases and subsequently reacted with acetylene [as described by H. Beller, et al., British Patent No. 641,437, issued in 1950; see *Chemical Abstracts*, Vol. 45, p 8044i (1950)]; ethylene oxide [as described by I. P. Zherebtsov and V. P. Lopatinskii, in *Izv. Tomsk. Politekt Inst.*, Volume 196, page 189, published in 1969; see *Chemical Abstracts*, Vol. 72, 111210 Z (1970)]; 2-chloroethanol/acetic anhydride [as described by R. G. Flowers, et al., published in the *Journal of the American Chemical Society*, Vol. 70, page 3019 (1948)]; vinyl chloride [as described by W. Reppe, et al., published in *Annalen*, Vol. 601, page 128 in 1956; see *Chemical Abstracts*, Vol. 51, 9584a (1957)]; and vinyl acetate [as described by V. P. Lopatinskii, et al., published in *Methody Poluch Khim., Reaktiv. Prep.*, Number 22, page 200 in 1970; see *Chemical Abstracts*, Vol. 77, 139714 (1972)]. Carbazole has also been reported to react with the tosylate of 2-chloroethanol to form β-chloroethylcarbazole which is subsequently treated with base to give N-vinyl carbazole [as described by T. Ishii and M. Hayaski, published in the *Journal of the Society of Organic Synthetic Chemists of Japan*, Vol. 7, page 41, in 1949; see *Chemical Abstracts*, Vol. 44, 3970i (1950)]. Carbazole has been reacted with ethylene and various vinyl ethers in the presence of catalysts to produce N-vinylcarbazole as reported by E. W. Stern and M. L. Spector, in U.S. Pat. No. 3,564,007, issued in 1971; K. Matsurshiro and T. Oda, Japanese Pat. No. 749,466, issued in 1974; [see *Chemical Abstracts*, Vol. 83, P148000j (1975)]; and V. A. Anfinogenor, et al., published in the *Zhurnal Org. Khim.* Vol. 14, page 1723 in 1978; see *Chemical Abstracts*, Vol. 90, 38764y (1979).

In addition, V. D. Filimonov, et al., described the addition of carbazole to acetaldehyde in the presence of an alcohol to produce the intermediate α-alkoxyethyl N-carbazoles which are subsequently contacted with chloride in pyridine to produce N-vinyl carbazole [see *Zhurnal, Org. Khim.*, Vol. 14, page 2607, in 1978; *Chemical Abstracts*, Vol. 90, 103763p (1979)].

Most of these reactions require isolation of intermediates, high pressures and temperatures, special equipment and/or long reaction times.

It is an object of this invention to describe a process for the preparation of substituted N-vinyl carbazoles.

It is a further object of this invention to describe a process that can be performed at atmospheric pressure in glassware, without the need for isolation of intermediates.

BRIEF SUMMARY OF THE INVENTION

In summary, the process of this invention comprises the preparation of various N-vinylcarbazoles by contacting an N-unsubstituted carbazole with a dihaloethane, optionally in an inert solvent using an alkaline halide as a facilitator, in the presence of a phase transfer catalyst followed by contact with an aqueous solution containing a highly basic agent, and recovery of the product by methods which are known in the art.

More specifically, this invention relates to a process for preparing N-vinyl carbazoles represented by the following formula:

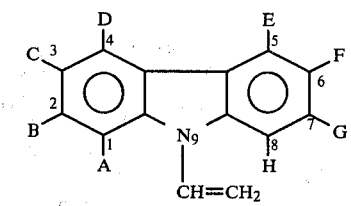

wherein:

substituents A, B, C, D, E, F, G and H are independently selected from the group consisting of hydrogen, fluorine, chlorine, bromine, iodine, methyl, ethyl, n-propyl, iso-propyl, butyl, amyl, iso-amyl, methoxy, ethoxy, nitro, cyano, methylamino, ethylamino, dimethylamino, diethylamino, and trifluoromethyl;

which process comprises:

(a) contacting an N-unsubstituted carbazole with a 1,2-dichloroethane in the presence of a phase transfer catalyst; and (b) treating with a highly basic agent to form the N-vinyl carbazole.

The process after step (b) may optionally include treatment of the solution with a mixture of a highly basic agent and an organic alcohol. Subsequent recovery of the N-vinylcarbazole so prepared can be by techniques known in the art. The numbers shown on the above formula identify the position of the carbazole ring structure according to the *Nomenclature of Organic Chemistry*, International Union of Pure and Applied Chemistry, 3rd Edition (1971).

The dichloroethane may be the solvent for the carbazole and thus function also as the reaction medium or, optionally, step (a) above may include a dipolar aprotic solvent and a facilitator, such as an alkaline halide.

Carbazoles

Almost any of the carbazoles which can be prepared by chemical routes known in the literature are useful in this invention. Generally, those carbazoles having the chemical substituents cited above are useful in the practice of this invention. Presently preferred compounds include carbazole, tetrahydrocarbazole, 3-chlorocarbazole, 3,6-dibromocarbazole, 3,6-dichlorocarbazole and 3-nitro-carbazole. Presently, the most preferred compound is carbazole.

Dihaloethanes

Dihaloethanes are useful as alkylating reagents in this reaction. Suitable compounds would be those represented by the following formula:

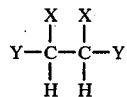

wherein: X and Y are independently selected from the group consisting of hydrogen, chlorine, iodine and bromine, provided that at least 2 Xs and Ys are halogen.

Mixtures of these compounds may also be used as reagents.

The dichloroethanes are preferred over the dibromoethanes. The presently preferred reagent is 1,2-dichloroethane wherein X is hydrogen and Y is chlorine in the formula shown above.

Solvents 1,2-Dichloroethane may be both a reagent and a solvent for this reaction. Any other dipolar or nonpolar aprotic solvent may be used in the practice of this invention, provided that it is inert and does not participate in the reaction. The use of these other solvents usually results in a slowing of the reaction rate and requires higher temperatures or longer reaction times to produce the desired carbazole in any quantity.

Typical dipolar or nonpolar solvents include, for example,
n-pentane
cyclopentane
n-hexane
isohexane
cyclohexane
n-heptane
isoheptane
cycloheptane
n-octane
iso-octane
cyclooctane
hexamethylphosphoramide
benzene
toluene
xylenes, o-, m-, and p-, and mixtures thereof.

Preferred solvents include toluene, hexane, and 1,2-dichloroethane. The presently preferred solvent is 1,2-dichloroethane.

Phase Transfer Catalysts

Phase transfer catalysts have been reported extensively and reviewed in the literature, for instance, by W. E. Keller, *Compendium of Phase Transfer Reactions and Related Synthetic Materials,* 1st Ed., Fluka, A. G., Switzerland 1979. These catalysts usually are alkyl or aryl ammonium compounds which can be represented by the following formula:

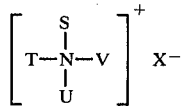

wherein:
N is nitrogen;
S, T, U, and V are independently selected from alkyl moieties containing from 1 to 10 carbon atoms and aryl groups selected from the group consisting of phenyl, tolyl, xylyl, naphthyl, benzyl, methoxyphenyl, chlorophenyl, chlorotolyl, chloroxylyl, and chloronaphthyl; and
X is a fluorine, chlorine, bromine, iodine and hydrogen sulfate (—HSO$_4$).

Presently preferred compounds include the alkyl substituted ammonium chlorides and bromides. More preferred compounds are tetrabutyl ammonium bromide and benzyltriethylammonium chloride. Such compounds are presently commercially available from the Aldrich Chemical Co., Inc. of Milwaukee, Wis., and the Hexcel Corporation, Inc. of Lodi, N.J.

Facilitators

Optionally, alkaline halides and mixtures thereof when added to the reaction mixture have been found to function somewhat as "facilitators" or "catalysts." These compounds appear to increase somewhat the rate of the chemical reaction by supplying a halide ion, X$^-$, to the reaction mixture. If omitted, the time for the reaction to go to completion is longer. However, when these compounds are not added, their lack can be compensated for by increasing the temperature and time of the reaction.

Compounds that are useful as facilitators include the alkaline halides. A presently preferred compound is sodium bromide.

Basic Agents

The basic agent in step (b) of this invention is believed to serve a dual function. It serves to: (1) deprotonate the carbazole and form a negatively charged nitrogen atom which is subsequently alkylated by the dihaloethane described herein; and (2) dehydrohalogenate the carbazole haloethane so formed in situ. Any strongly or highly basic solution or ion exchange resin capable of performing these functions are useful in this invention.

Presently preferred basic agents include the alkaline and alkaline earth hydroxides, and mixtures thereof. Presently more preferred basic agents are sodium hydroxide and potassium hydroxide. A presently most preferred basic agent is sodium hydroxide.

Normally, the basic agents of this invention will be aqueous solutions which can perform the functions described herein. These solutions can range from 1–90% concentration of the basic agent. A more preferred range is 30–70% of alkaline hydroxide in water. The most preferred basic agent is a 50% solution of sodium hydroxide in water.

In-situ Alkoxides

In the process shown above after step (b), a subsequent step may further include treatment of the heterogenous solution or crude product with an alkaline or alkaline earth hydroxide in an organic alcohol. It is believed that this basic solution may produce in situ reactive alkoxides which serve to complete the dehydrohalogenation of the β-haloethyl carbazole to produce the N-vinyl carbazole. The purification of the vinyl carbazole from precursors and other reaction products is therefore facilitated.

The alkaline or alkaline earth hydroxides useful in this step are the same as described earlier under the heading "Basic Agents." A presently preferred hydroxide is potassium hydroxide. The concentration of this hydroxide may range from 10–90 percent by weight of the organic alcohol. A presently preferred range is between 20 and 30 percent by weight of the organic alcohol.

The organic alcohol useful to produce this in situ alkoxide may be any of the familiar organic alcohols. Usually the aliphatic, cycloaliphatic, arylaliphatic and aryl alcohols will contain between 1 and 12 carbon atoms. Typical alcohols include:
methanol
ethanol 1-propanol
2-propanol (iso)
1-butanol
2-butanol
t-butanol
1-pentanol
2-pentanol
3-pentanol
1-hexanol
2-hexanol
1-heptanol
2-heptanol
1-octanol
2-octanol
1-decanol
1-dodecanol
cyclohexanol
benzyl alcohol
phenol
1-naphthanol
2-naphthanol, and
mixtures thereof.

Presently preferred alcohols are lower aliphatic alcohols containing 1-4 carbon atoms.

A presently preferred combination is a 20-30 percent by weight of potassium hydroxide in 2-propanol.

DESCRIPTION OF SPECIFIC EMBODIMENTS

The following specific description is given to enable those skilled in this art to more clearly understand and practice the present invention. It should not be considered as a limitation upon the scope of the invention but merely as being illustrative and representative thereof.

EXAMPLE 1

Step A: A mixture of carbazole (ALDRICH, 1.0 g, 6 mmol), tetrabutyl ammonium bromide (ALDRICH, 0.2 g, 0.6 mmol), sodium bromide (0.6 g, 6 mmol), and 1,2-dichloroethane (20 ml, 0.25 mol) is added to a 250 ml round-bottom glass flask with magnetic stirring under a nitrogen blanket at room temperature.

Step B: A solution of sodium hydroxide (MALLINCKRODT, 10 g, 0.25 mol) is slowly added, and stirring is continued as a small rise in temperature is observed. After 18 hours, thin layer chromatographic analysis (silica gel, 40% acetone/hexane) shows a compound with the same $R_f$ value as carbazole but which apears green upon treatment with light having a long wave length.

Step C: The brown mixture is diluted with 50 ml of water, separated, and the organic layer is washed twice with two 50 ml portions of water. The solvent is removed using a water aspirator, producing about a 100% yield of crude product.

Step D: After stirring the crude product with 20 ml of isopropyl alcohol and 5 g of potassium hydroxide, the mixture is refluxed for 2.5 hours. Analysis by thin layer chromatography (silica gel, 40% acetone/hexane) shows no β-chloroethylcarbazole is present.

Step E: The solvent is removed using water aspiration, and the residue is stirred with 50 ml of water and filtered to produce 1.0 g of a tan solid, yield 85 percent or more.

Step F: When thin layer chromatographic analysis (silica gel, 40% acetone/hexane) shows the presence of a minor impurity, the tan solid is dissolved in 25 ml of ethanol, stirred with Darco (charcoal) and filtered to produce a very pale tan solution. When recrystallized from hot ethanol, about 0.5 g (about a 50% yield) of N-vinyl carbazole as colorless flakes, mp 62°-63° C. are obtained.

The nuclear magnetic resonance spectrum is identical to the spectrum of N-vinylcarbazole.

EXAMPLES 2-6

In Examples 2-6, the quantities of material shown on the left side of the table are added at the particular Step (A-F) noted, as is described in Example 1. Any additional changes are noted as footnotes.

TABLE 1

| | Preparation of N-Vinyl carbazoles | | | | | |
|---|---|---|---|---|---|---|
| Steps | Chemical | 2 Mole | 3 Mole | 4 Mole | 5 Mole | 6 Mole |
| A. | Carbazole | 1. | 1. | 1. | 1. | 1. |
| A. | 1,2-dichloroethane | 42. | 42. | 42. | 14. | 42. |
| A. | Sodium Bromide | 1. | 1. | 0.0 | 1. | 1. |
| A. | Tetrabutyl Ammonium Bromide | 0.01 | 0.20 | 0.1 | 0.01 | 0.01 |
| B. | Sodium Hydroxide in Water | 42. | 42. | 42. | 14. | 21. |
| C. | Water wash | 463. | 463. | 463. | 463. | 463. |
| D. | Isopropyl Alcohol | 43. | 43. | 43. | 43. | 43. |
| D. | Potassium Hydroxide | 15. | 15. | 15. | 15. | 15. |
| E. | Water | 463. | 463. | 463. | 463. | 463. |
| F. | Ethanol | 71. | 71. | 71. | 71. | 71. |

EXAMPLE 7

This example is essentially performed as is described in Example 1, but on a scale about 50 times that of Example 1.

Carbazole (BIDDLE, 50.0 g, 0.3 mol), 1,2-dichloroethane (1 l, about 12.7 mol), sodium bromide (FISCHER, 30.0 g, 0.29 mol), tetrabutyl ammonium bromide (add slowly—ALDRICH, 1 g, 3.1 mmol), and 1 kg of a 50% aqueous sodium hydroxide solution are added under nitrogen to a dry 2-l 3-necked round bottom flask fitted with a mechanical stirrer, thermometer and gas inlet tube. The reaction mixture slowly warms without heating from room temperature to about 55° C. After 5 hours, the reaction mixture cools to about 42° C. After three days with heating between 30° and 50° C., the reaction mixture is cooled to room temperature, diluted with 1.25 l. of water, and separated; the organic phase is washed three times with 1 l. of water; and the solvent is removed using a water aspirator and steam bath. The tan residue is contacted with 500 ml of isopropyl alcohol and 100 g of potassium hydroxide, heated at reflux for 18 hours, and 500 ml of isopropyl alcohol and 100 g of potassium hydroxide is added. After 6.5 hours, analysis using thin layer chromatography (silica gel, 40% acetone/hexane) showed very little, if any, β-chloroethylcarbazole remaining. The isopropyl alcohol solvent is removed using a water aspirator with steam heating.

The residue is treated with 2 l of water, filtered, washed with water to produce 61.8 g of a wet brown solid. This solid was recrystallized from 500 ml of hot methanol using Darco G-60 (carbon), filtering, concentrating to 450 ml, and cooling to 5° C. Upon filtration, 31.6 g of pale cream-colored crystals having a mp of 62°-63° C. is obtained. Analysis by thin layer chromatography (silica gel, 40% acetone/hexane) shows minor impurities.

600 Ml of water is added to the filtrate and allowed to stand. Subsequent filtration yields about 10.7 g of N-vinyl carbazole as a yellow tan solid.

While the present invention has been described with reference to the specific embodiments thereof, it should be understood by those skilled in this art that various changes may be made and equivalents may be substituted without departing from the true spirit and scope of the invention. In addition, many modifications may be made to adopt a particular situation, material, or composition of matter, process, process step or steps, or the present objective to the spirit of this invention without departing from its essential teachings.

What is claimed is:

1. A process for the preparation of a N-vinylcarbazole represented by the following formula:

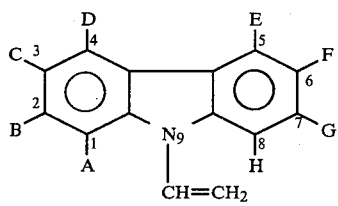

wherein:
substituents A, B, C, D, E, F, G and H are independently selected from the group consisting of hydrogen, fluorine, chlorine, bromine, iodine, methyl, ethyl, n-propyl, iso-propyl, butyl, amyl, iso-amyl, methoxy, ethoxy, nitro, cyano, methylamino, ethylamino, dimethylamino, diethylamino and trifluoromethyl;
which process comprises:
(a) contacting the appropriately N-unsubstituted carbazole with a 1,2-dihaloethane in the presence of a phase transfer catalyst; and
(b) treating with a basic agent to form the corresponding N-vinylcarbazole.

2. The process of claim 1 wherein step (a) optionally includes a non-polar solvent, a dipolar aprotic solvent, or mixtures thereof, and, optionally, one or more alkaline halides.

3. The process of claims 1 or 2 wherein after step (b) the process includes treatment with a mixture of an alkaline hydroxide and an organic alcohol.

4. The process of claim 3 wherein said alkaline hydroxide is potassium hydroxide and said organic alcohol is 2-propanol.

5. The process of claim 2 wherein said alkaline halide is sodium bromide.

6. The process of claim 1 wherein said N-unsubstituted carbazole is 3-nitrocarbazole, that is, substituent C is nitro and substituents A, B, and D-H are hydrogen.

7. The process of claim 1 wherein said N-unsubstituted carbazole is 3,6-dichloro-N-vinylcarbazole, that is, substituents C and F are chlorine and substituents A, B, D, E, G, and H are hydrogen.

8. The process of claim 1 wherein said N-unsubstituted carbazole is 3-chlorocarbazole, that is, substituent C is chlorine and substituents A, B and D-H are hydrogen.

9. The process of claim 1 wherein said N-unsubstituted carbazole is carbazole, that is substituents A-H are all hydrogen.

10. The process of claim 9 wherein said phase transfer catalyst is tetrabutyl ammonium bromide.

11. The process of claim 1 wherein said phase transfer catalyst is tetrabutyl ammonium bromide.

12. The process of claim 1 wherein said basic agent is an aqueous alkaline hydroxide solution.

13. The process of claim 1 wherein said basic agent is about a 50% aqueous solution of sodium hydroxide.

14. The process of claim 2 wherein said basic agent is an aqueous alkaline hydroxide solution.

15. The process of claim 2 wherein said basic agent is about a 50% aqueous solution of sodium hydroxide.

16. A process for the preparation of N-vinylcarbazole which process comprises:
(a)(i) contacting an approximately molar solution of carbazole in 1,2-dichloroethane with a catalytic amount of tetrabutyl ammonium bromide for about 0 to 0.5 hours;
(ii) adding a 40–60 percent by weight of an aqueous sodium hydroxide solution for about 24–72 hours at a temperature between about 20° and 100° C., and;
(b) recovering said N-vinylcarbazole by removal of the 1,2-dichloroethane.

17. A process of claim 16 wherein the solution in step (a)(i) includes a nonpolar solvent, a polar aprotic solvent, or mixtures thereof, and, optionally, one or more alkaline halides.

18. The process of claim 17 wherein said alkaline halide is sodium bromide.

19. The process of claim 16 wherein after step (b) the process includes treatment with a mixture of an alkaline hydroxide and an organic alcohol.

20. The process of claim 19 wherein said alkaline hydroxide is potassium hydroxide and said organic alcohol is 2-propanol.

* * * * *